United States Patent
Shan et al.

(10) Patent No.: US 7,422,578 B2
(45) Date of Patent: Sep. 9, 2008

(54) CONNECTING OSTOMY DEVICE

(75) Inventors: Nicolas Shan, Vincennes (FR); Alexandre Macquin, Gif sur Yvette (FR)

(73) Assignee: B. Braun Medical SAS, Boulogne Billancourt (FR)

( * ) Notice: Subject to any disclaimer, the term of this patent is extended or adjusted under 35 U.S.C. 154(b) by 73 days.

(21) Appl. No.: 10/571,783

(22) PCT Filed: Sep. 17, 2004

(86) PCT No.: PCT/FR2004/002360

§ 371 (c)(1),
(2), (4) Date: Mar. 14, 2006

(87) PCT Pub. No.: WO2005/025466

PCT Pub. Date: Mar. 24, 2005

(65) Prior Publication Data

US 2007/0005032 A1 Jan. 4, 2007

(30) Foreign Application Priority Data

Sep. 18, 2003 (FR) ................................. 03 10982
Feb. 13, 2004 (FR) ................................. 04 01491

(51) Int. Cl.
*A61F 5/44* (2006.01)
(52) U.S. Cl. ................. 604/342; 604/332; 604/343; 604/339; 604/338; 604/334

(58) Field of Classification Search ................ 604/332, 604/342, 339, 338, 344
See application file for complete search history.

(56) References Cited

U.S. PATENT DOCUMENTS

| 4,359,051 | A | * | 11/1982 | Oczkowski | 604/344 |
|---|---|---|---|---|---|
| 4,636,205 | A | | 1/1987 | Steer | |
| 4,846,820 | A | | 7/1989 | Jensen | |
| 4,894,058 | A | * | 1/1990 | Jensen | 604/332 |
| 5,257,981 | A | * | 11/1993 | Takahashi | 604/342 |
| 5,312,381 | A | * | 5/1994 | Brooks | 604/338 |
| 5,520,670 | A | * | 5/1996 | Blum | 604/338 |
| 5,843,053 | A | * | 12/1998 | Steer | 604/342 |
| 6,033,390 | A | * | 3/2000 | von Dyck | 604/332 |
| 6,206,864 | B1 | | 3/2001 | Kavanagh et al. | |

FOREIGN PATENT DOCUMENTS

| DE | 299 15 282 | 12/1999 |
|---|---|---|
| EP | 0 598 625 | 5/1994 |
| EP | 0 747 026 | 12/1996 |
| FR | 2 396 541 | 2/1979 |
| JP | 2000-271162 | 10/2000 |

* cited by examiner

*Primary Examiner*—Tatyana Zalukaeva
*Assistant Examiner*—Ilya Y Treyger
(74) *Attorney, Agent, or Firm*—Young & Thompson

(57) ABSTRACT

A connecting ostomy device for coupling a collecting bag to a fixing device (10) includes a first joining part (16) connected to the fixing device and a second joining part (12) connected to the collecting bag. The joining parts interact by adhesion in a plane practically perpendicular to the axes of orifices (14) of the collecting bag of the fixing device in such a way that the transmission of the bag weight and the impermeability thereof are ensured by adhesion. The additional fixing elements (18, 20) ensure the alignment of the orifices (14) of the fixing device (10) and the collecting bag in a position thereof which is practically determined before the removal of the protective film from an adhesive surface. The connecting device is used for ostomy.

13 Claims, 6 Drawing Sheets

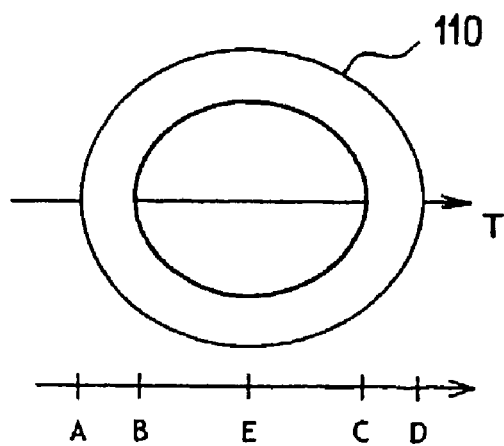
FIG_12
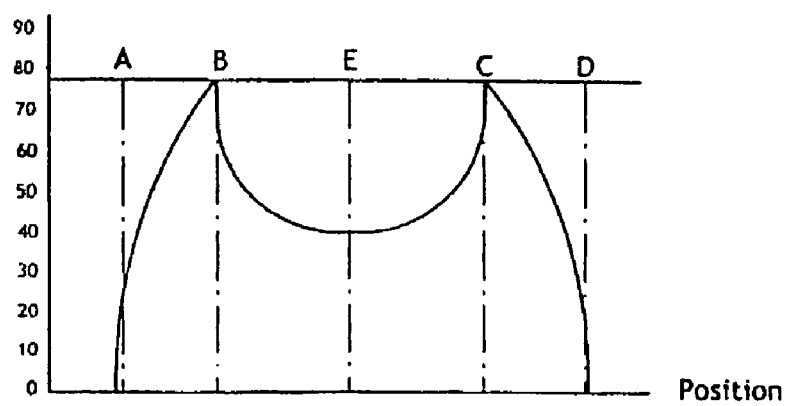
FIG_13
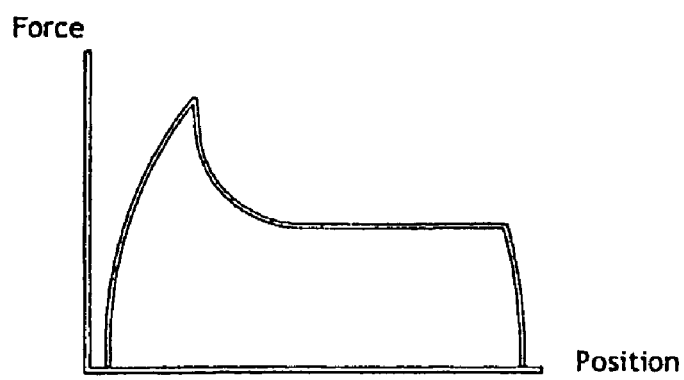
FIG_15

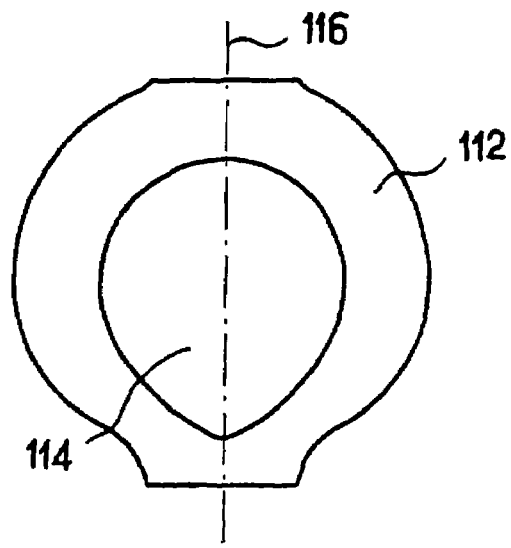
FIG_14
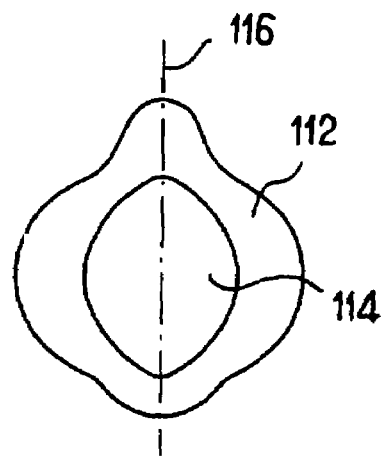
FIG_16
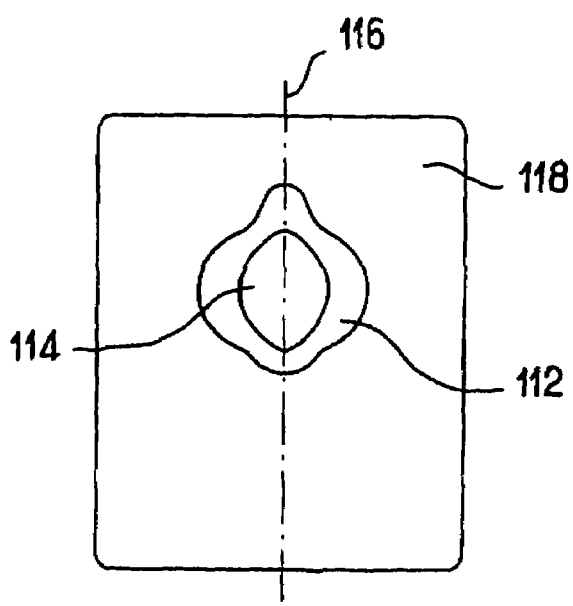
FIG_17

CONNECTING OSTOMY DEVICE

BACKGROUND OF THE INVENTION

1. Field of the Invention

The invention relates to ostomy devices which are constructed in two parts.

2. Description of the Related Art

Ostomy devices in two parts comprise a fixing or support device which is adhesively-bonded to the skin around an ostomy, and a removable pouch which is intended to be connected to the fixing device. The advantage of these two-part devices is that a single adhesive-bonding of a fixing device around the ostomy allows the successive use of a plurality of pouches, generally at least three. Although it is possible to produce materials which constitute gums which are capable of absorbing humidity and which are non-allergenic, the detaching operation still subjects the skin to stresses which it is desirable to spread over time.

Various connections have therefore been produced which are intended to fix a collection pouch in a fluid-tight manner to a fixing device. There are substantially two generic types of such connection, a mechanical type and an adhesive type.

There are a number of variants of the connections of the mechanical type. Three are described which are representative of this range.

In a first example of a mechanical connection, a fixing device having a gum disc carries a ring having a plurality of lips which delimit a channel in which a wall of a ring carried by a pouch is accommodated. The mechanical strength is provided by co-operation of lips of the two rings, the sealing is provided by the contact of a lip of the ring with the body of the ring, and the guiding for the positioning is provided when a ring is accommodated on the other ring, the engagement being provided simply by applying a force to the rings.

A second known mechanical connection device is such that a fixing device and a pouch each comprise a ring, the rings having lips which are intended to fit into each other in order to provide both the mechanical strength and sealing.

A third known mechanical connection has a small pivoting lever which rotates a blocking device which, after two rings are engaged one on the other, blocks them by means of locking in order to provide a very high level of strength.

All these known mechanical devices have the advantage of allowing the co-operation of two rings only when they are correctly centred one on the other, with the result that the positioning of the two connection portions is excellent.

However, they do have disadvantages. The sealing is obtained by means of contact of one or more lips with a complementary surface. In order for a lip to provide a good level of sealing, it must have a good level of resilience, that is to say, it must either be very thin or be formed from a relatively flexible material. If the material of the ring, and therefore the lip, is flexible, the mechanical strength obtained is reduced. If the material of the ring is rigid and hard, the connection as a whole constitutes a rigid element which brings about a degree of discomfort.

Furthermore, all the elements having lips must comply with strict tolerances; they are formed by means of injection and are therefore costly.

Given the disadvantages of these mechanical connections, attempts have been made to use connections which function by means of adhesive-bonding. Connections have therefore been produced in which an adhesive disc, which is fixedly joined to the pouch and which is protected by a protective paper, is adhesively-bonded to a strip of a device for fixing to the user. The advantages of such a connection by means of adhesive-bonding are clear: the assembly can be flexible and thin, and can therefore provide a high level of comfort and, as the adhesive-bonding surface can be extensive, an excellent level of sealing and mechanical strength can be provided.

However, this connection by means of adhesive-bonding presents a problem: it is difficult to position an adhesive portion of the pouch on the fixing device whilst ensuring the alignment of the holes of these two elements.

Given the very adhesive nature of the connection portion of the pouch, as soon as it has begun to adhesively-bond to an opposing portion, it is no longer possible to displace the two portions relative to each other. Furthermore, if the two connection portions are flexible, and therefore provide an advantage in terms of comfort, the uniform application of the two portions one to the other presents problems owing to this very flexibility.

According to document FR-2 396 541, an ostomy pouch connection is already known such that a fixing device comprises a circular end-piece which extends from the device around the hole thereof and which is surrounded by an adhesive-bonding strip and, at the outer side thereof, hook and loop type fixing elements. The pouch has a connection portion which comprises a circular adhesive surface which surrounds a hole and, around this adhesive surface, hook and loop type fixing elements. When it is used, the end-piece of the fixing device is introduced into the hole of the pouch before the adhesive surface comes into contact with the adhesive strip or the hook and loop type fixing elements move into co-operation. The holes are therefore well aligned. A first disadvantage of this device is that the end-piece, in order to be effective, must have a specific length: it confers a high level of rigidity on the fixing portion and therefore brings a considerable level of discomfort. In particular, as the adhesive surface surrounds the end-piece, the paper which protects it must be removed before the end-piece moves into the hole of the pouch. The end of the end-piece is therefore necessarily in contact with the exposed adhesive surface before being introduced into the hole of the pouch. If the adhesive is very effective, it is almost impossible to detach it without significantly damaging the adhesive: this is without doubt the reason why the function of mechanical strength of the pouch is not provided by the adhesive surface, but instead by the hook and loop type fixing elements.

BRIEF SUMMARY OF THE INVENTION

The invention relates to the solution to this problem of mutually positioning the two connection portions in the case of an adhesive-bonding operation.

More precisely, according to the invention, the fixing portion and the pouch can first be fixed at least partially one to the other before the adhesive surface is separated from the protective paper thereof. In this manner, when the protective paper is removed, the fixing device and the pouch can assume only one position in which the holes thereof are aligned.

The invention thus relates to an ostomy device connection which is intended to connect a collection pouch to a fixing device which is intended to be adhesively-bonded to the skin of a user, the connection serving to transmit the weight of the collection pouch to the fixing device, to position the pouch relative to the fixing device so that a hole of the fixing device is in communication with a hole of the collection pouch, and to provide sealing between the collection pouch and the fixing device, the connection comprising a first connection portion which is fixedly joined to the fixing device and a second connection portion which is fixedly joined to the collection pouch, one of the connection portions having an adhesive surface which is covered before use by a removable protective sheet and the other connection portion having an adhesion strip, so that the two connection portions can co-operate with each other by means of adhesive-bonding in a plane which is practically perpendicular relative to the axes of the holes of the pouch and the fixing device, and the transmission of the weight of the collection pouch and the sealing between the fixing device and collection pouch are provided by means of adhesive-bonding; the collection pouch and the fixing device comprise complementary fixing elements which are intended to limit the possibilities for relative displacement of the pouch and the fixing device so that the two connection portions have practically only one possible relative position when they are adjacent, this position corresponding to the alignment of the holes of the fixing device and the collection pouch. According to the invention, the protective sheet of the adhesive layer has the feature of being able to be detached from the adhesive surface after the complementary fixing elements have been brought into co-operation.

In one embodiment, the complementary fixing elements form an articulation device which delimits a pivot axis remote from the holes of the fixing device and the collection pouch, the protective sheet being practically entirely at only one side of the pivot axis.

In another embodiment, the complementary fixing elements comprise at least two push-buttons which are aligned along an axis.

In another embodiment, the complementary fixing elements comprise two elements which are fixedly joined to the fixing device and the pouch, respectively, and which are able to provide mutual fixing by means of magnetic attraction.

In another embodiment, the complementary fixing elements comprise a tongue which is fixedly joined to a first portion of the connection and a curved member which is fixedly joined to the other portion of the connection.

In another embodiment, the complementary fixing elements comprise a relatively rigid lug which is fixedly joined to a portion of the connection and which is intended to engage in a housing which is fixedly joined to the other portion of the connection.

In another embodiment, the complementary fixing elements comprise shaped portions of hook and loop type fabric which are fixedly joined to each of the connection portions.

In another embodiment, the complementary fixing elements comprise at least a first element which is arranged on a first connection portion, and a plurality of second elements which are arranged on the other connection portion and which have positions which are angularly spaced-apart around the hole of the corresponding connection portion, the first element being able to co-operate with any one of the second elements. For example, the portion carrying the tongue may comprise a plurality of tongues having positions which are angularly spaced-apart around the hole thereof.

In a variant, the connection comprises auxiliary elements for fixing the connection portions.

In another embodiment, the protective sheet of the adhesive layer comprises at least two portions which are folded in the form of a folder whose folds are adjacent on the adhesive surface so that this adhesive surface is completely covered and the flap which is not adhesively-bonded to the adhesive surface has a gripping lug which extends beyond the limits of the adhesive surface.

In another embodiment, the connection comprises an auxiliary device for retaining the connection portions by means of fitting.

The fixing device preferably comprises a flexible disc which has a practically central hole which is intended to surround an ostomy, the disc being intended to be adhesively-bonded to the skin of a user around an ostomy, and a strip which is fixed to the disc in a fluid-tight manner around the hole.

According to advantageous variants, since the portion having the adhesive surface is intended to be detached in one direction after use, the configuration of this adhesive surface is such that the total length of the face for detaching by means of peeling, in a direction which is generally perpendicular relative to the detaching direction, is modulated so that it is substantially constant over the majority of the length of the portion having the adhesive surface in the detaching direction.

According to variants, the portion having the adhesive surface is completely covered with adhesive, or the portion having the adhesive surface is only partially covered with adhesive.

BRIEF DESCRIPTION OF THE DRAWING FIGURES

Other features and advantages of the invention will be better understood from a reading of the following description of embodiments, given with reference to the appended drawings, in which:

FIG. 12 illustrates a connection element which can be the disc which has an adhesive surface and which is fixedly joined to the pouch of FIGS. 1 to 3;

FIG. 13 is a graph illustrating the variation of the total length of the peeling face, in a direction perpendicular relative to a detaching direction T, in accordance with the position on the face of the connection element, and it also illustrates the variation of the detaching resistance force;

FIG. 14 illustrates the adhesive surface of a connection element which has a form defined according to the invention;

FIG. 15 illustrates the variation of the detaching resistance force of the connection element according to the invention illustrated in FIG. 14;

FIG. 16 illustrates the adhesive-bonding surface of another connection element having a form which is defined according to the invention; and FIG. 17 illustrates an ostomy pouch which is provided with the connection element of FIG. 16.

DETAILED DESCRIPTION OF THE PREFERRED EMBODIMENTS

Figure 1:
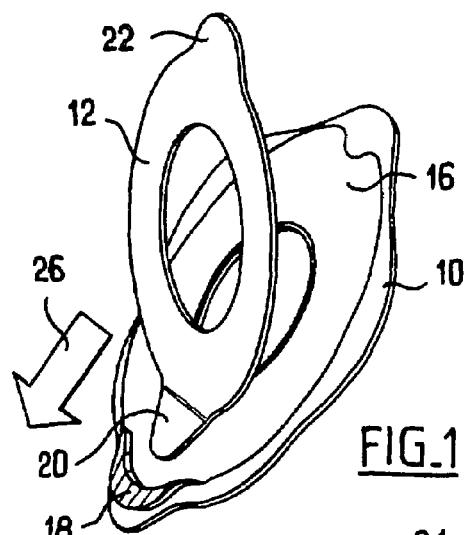
FIG. 1 is a perspective view of an ostomy connection according to the invention, at an initial positioning stage, the portions of the pouch other than the connection being omitted for reasons of clarity of illustration.
Figure 2:
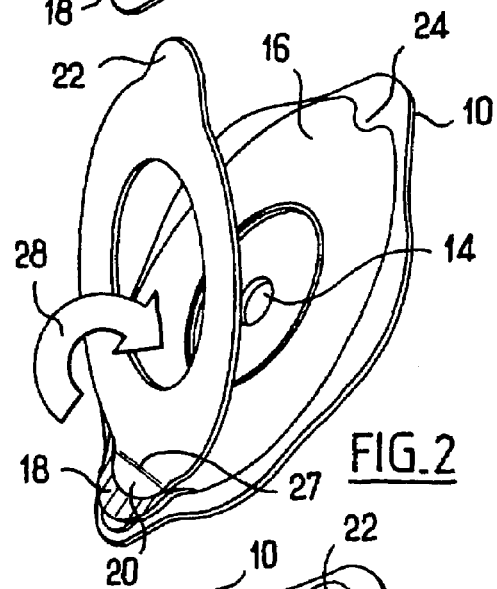
FIG. 2 is a perspective view of the ostomy connection of FIG. 1 at a subsequent positioning stage.
Figure 3:
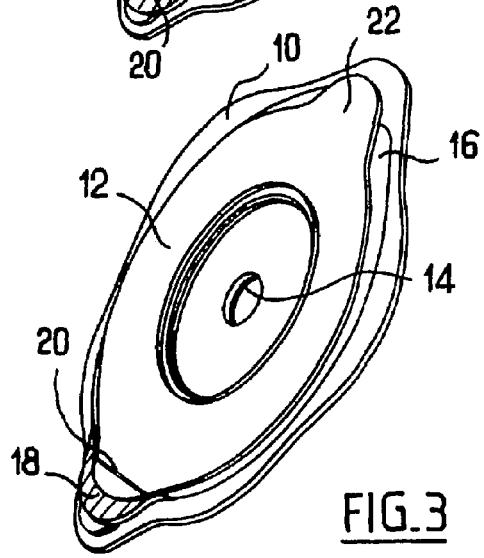
FIG. 3 is a perspective view of the ostomy connection of FIG. 1 after the positioning has been carried out.

The ostomy connection illustrated in FIGS. 1 to 3 comprises a portion which is fixedly joined to a fixing device 10 and another connection portion 12 which is associated with a pouch (not illustrated).

The fixing device 10 comprises a gum disc and a strip 16. In known manner, the gum contains a polymer and hydrocolloids, and it allows robust fixing to the skin of the user around an ostomy.

At the side opposite the adhesive portion of the gum, the strip 16 is fixed to the disc around a hole 14. This strip constitutes a first connection portion. It comprises a flat and flexible portion and, at one side of the periphery thereof, a curved member 18. It is advantageously formed from polyethylene, a copolymer of ethylene and vinyl acetate, or a similar polymer which can be readily moulded in order to form the curved member 18 and welded to the gum disc around the hole 14 and over only part of the distance between the edge of the hole and the periphery of the strip which is therefore free.

The connection portion 12 of the pouch surrounds a hole and has a tongue 20. The face of the portion 12 that is not visible in FIGS. 1 to 3 is covered with an adhesive which is itself covered with a protective sheet, for example, a protective paper containing silicone. A lug 22 allows the connection portion 12 to be retained during detaching. The strip 16 preferably has, opposite the location which the lug 22 must occupy, a notch 24 which forms a recess which facilitates the gripping of the lug between two fingers.

The use of the ostomy connection will now be described with reference to FIGS. 1 to 3. The user, to which the fixing device 10 is adhesively-bonded, grips a pouch provided with the connection portion 12 which carries, over the entire adhesive face thereof, a protective paper which is preferably cut between the tongue 20 and the remainder of the connection portion 12. He introduces the tongue 20 beneath the curved member 18 as indicated by the arrow 26. He can carry out the operation progressively and restart it as many times as desired until the tongue has been completely introduced beneath the curved member. At this time, the connection portion 12 can no longer be displaced other than by pivoting about the axis 27 which separates the tongue from the remainder of the portion 12.

At this time, the user holding the pouch with one hand grips, with his other hand, the protective paper which itself preferably has a protruding lug (not illustrated). He removes this paper by means of peeling. He then has only to pivot the connection portion 12 which is adhesively-bonded in a completely aligned position to the strip 16.

The significant feature is that it is possible to position the two connection portions in a position which provides the alignment of the holes before removing the protective paper, so that the adhesive surface can be adhesively-bonded only to the strip 16.

People who have to carry such ostomy pouches sometimes wish to orientate the pouch body differently depending on whether it is carried during the day (with the person upright or seated) or during the night (with the person lying down). The connection described with reference to FIGS. 1 to 3 allows only a single orientation.

In one variant (not illustrated), the connection portion 12 of the pouch comprises a plurality of tongues, for example, three, which are spaced apart at intervals of 45° or 60°. The pouch can thus be orientated downwards during the day and towards the right or the left during the night.

It should be noted that the adhesive-bonding surface is very extensive since it covers the entire surface between the central hole and the circular periphery of the strip 16 or the connection portion 12. This adhesive-bonding provides, in known manner, a very good level of sealing and a very good level of mechanical strength.

These properties are obtained because the strip 16 and the connection portion 12 are completely centred. It can readily be envisaged that, if the two portions were off-centre, on the one hand, the surface for adhesive-bonding and therefore mechanical strength, would be reduced and, on the other hand, the probability of leakage in the region of the adhesively-bonded portion having a relatively small width would be high.

Figure 4A:
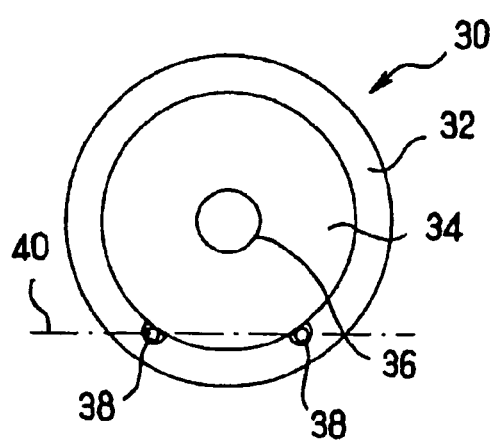
FIGS. 4a and 4b illustrate a fixing device and a pouch in which the complementary fixing elements are push-buttons, respectively.
Figure 4B:
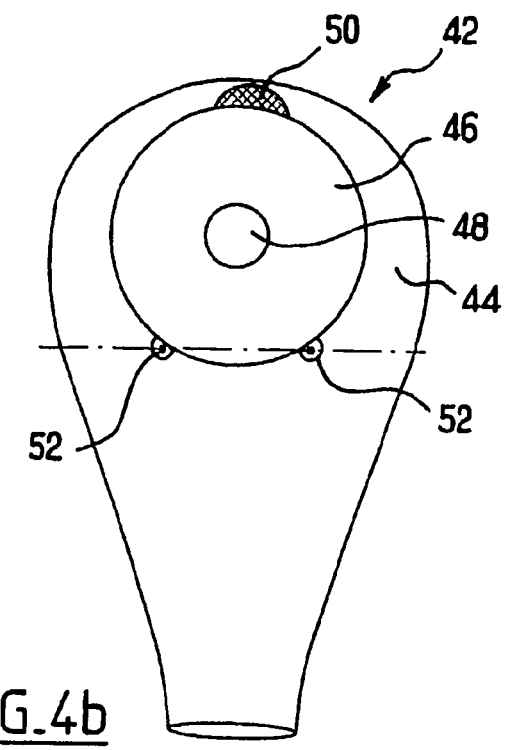

FIGS. 4a and 4b illustrate, in another embodiment, an ostomy device comprising a fixing device 30 and a pouch 42, respectively, which can be connected in a fluid-tight manner by means of a connection according to another embodiment of the invention.

The fixing device 30 comprises a gum disc 32. In known manner, this gum contains a polymer and hydrocolloids, and it allows robust fixing to the skin of the user around an ostomy.

At the side opposite the adhesive portion of the gum 32, a strip 34 is fixed to the disc 32 around the hole 36. This strip constitutes a first connection portion.

It is advantageously formed from polyethylene, copolymer of ethylene and vinyl acetate, or a similar polymer which can be readily welded to the disc 32, around the hole 36 and over only part of the distance between the edge of the hole and the periphery of the strip which is therefore free.

The pouch 42 has a body 44 and a connection portion 46 which surrounds a hole 48. A lug or ear 50 allows the connection portion 46 to be retained during detaching.

According to the invention, complementary fixing elements are constituted by two push-buttons 38, 52 which each have a portion which is fixed to the fixing device 30 and another portion which is fixed to the pouch 42. In the embodiment illustrated, the female portions of the push-buttons 38 are fixed to the edge of the strip 34 and the male portions of the push-buttons 52 are fixed to the edge of the connection portion 46 which forms an adhesive surface. The push-buttons 38, 38 and 52, 52 thus delimit a pivot axis 40.

During the positioning, since the fixing device has already been adhesively-bonded to the skin of the user, the connection portion 46, which has an adhesive surface which is protected by a protective paper, is moved closer, with the lower portion thereof, to the push-buttons 38 so that the male portions 52 can be attached to the female portions 38. The user can readily bring the push-buttons into co-operation since he can associate them without looking, by means of detection using touch. From this time, the upper portion of the pouch 42 can be displaced relative to the fixing device 30 only by means of pivoting about the axis 40.

The user then removes the protective paper from the adhesive connection portion 46 and, by pivoting upwards about the axis 40, presses the adhesive surface against the strip 34 of the fixing device. Taking into account the relative rigidity of the strip 34 and the connection portion 46, the two portions are adhesively-bonded to each other whilst being completely centred, that is to say, the hole 36 of the fixing device is located precisely opposite the hole 48 of the pouch.

Figure 5A:
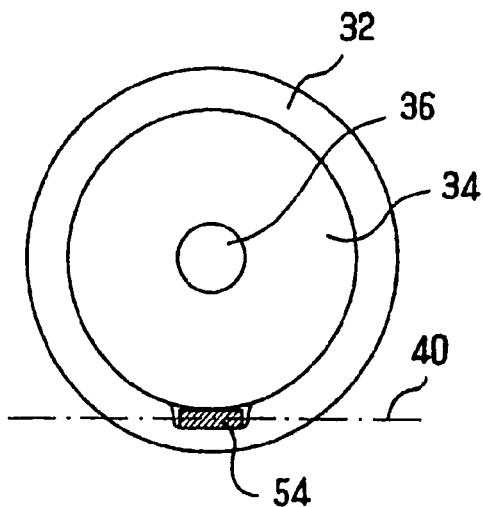
FIGS. 5a and 5b illustrate a fixing device and a pouch in which the complementary fixing elements are magnetic elements, respectively.
Figure 5B:
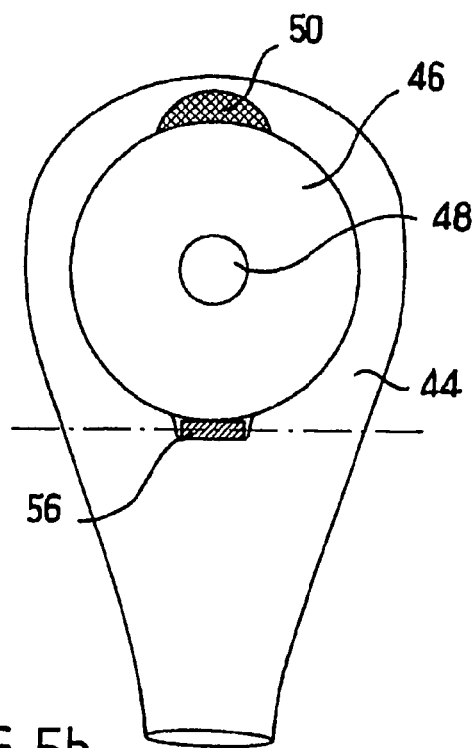

FIGS. 5a and 5b illustrate a similar device in which the role of the push-buttons 38, 52 is performed by two small magnets 54, 56, that is to say, they delimit a pivot axis in the direction of the length thereof (40 in the Figure). The result obtained is similar to that provided by the device of FIGS. 4a and 4b. It should also be noted that the presence of a gripping lug or ear 50 allows the pouch to be readily separated from the fixing device when the pouch has to be separated.

In FIGS. 5a to 5b, as in the following Figures, identical references have been used to those of FIGS. 4a and 4b to refer to the same elements.

Figure 6A:
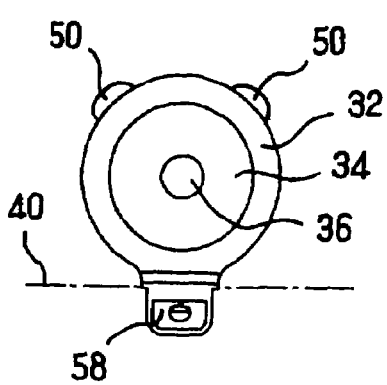
FIGS. 6a and 6b illustrate a fixing device and a pouch in which the complementary fixing elements are formed by a fixing means having male and female elements, respectively.
Figure 6B:
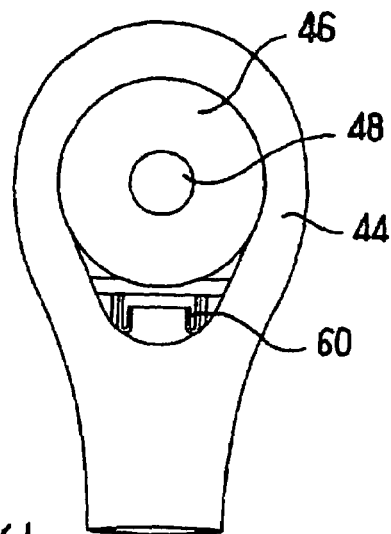

FIGS. 6a and 6b illustrate an embodiment in which complementary fixing elements are constituted by a resilient clip 58 which is intended to be accommodated in a guide 60 which is delimited by two lateral rails. When the pouch 42 has to be positioned on the fixing device, the female guiding portion 60 which is intended to co-operate with the clip 58 is slid thereon and thus engages in a resilient manner. The user preferably hears the engagement noise, such as a click, which informs him that the complementary fixing elements are in position. Then, by means of rotation about the axis 40, after the protective paper has been removed from the surface 46, this adhesive surface is pressed onto the strip 34 of the fixing device. In this embodiment, gripping hooks 50 have been illustrated on the fixing device.

Of course, the clip can be replaced by numerous devices having similar functions, such as a pincer which fastens onto a shaft, or a gripping member which slides in a channel. The significant feature is the definition of an axis for the rotation of the pouch relative to the fixing device.

In the embodiments which have been described above, the adhesive surface of the pouch is brought against the co-operating surface of the fixing portion by means of rotation about a pivot axis which is offset laterally relative to the holes. It is possible to keep the pouch portion provided with the adhesive surface remote from the fixing support except for in the region of the pivot axis at the beginning of positioning. Owing to this spacing-apart, in these embodiments in which the pivot axis is remote from the holes, it is even possible to remove, completely or partially, the protective paper from the adhesive surface of the pouch before the complementary fixing elements are brought into co-operation.

Figure 7A:
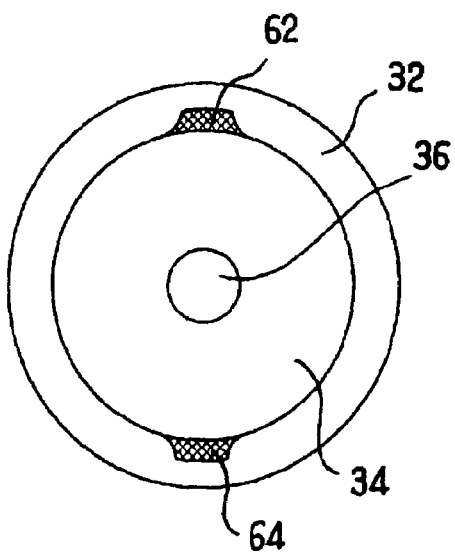
FIGS. 7a and 7b illustrate a fixing device and a pouch in which the complementary fixing elements are hook and loop type fixing elements, and the protective sheet of the adhesive layer comprises two portions which are folded in the manner of a folder, respectively.
Figure 7B:
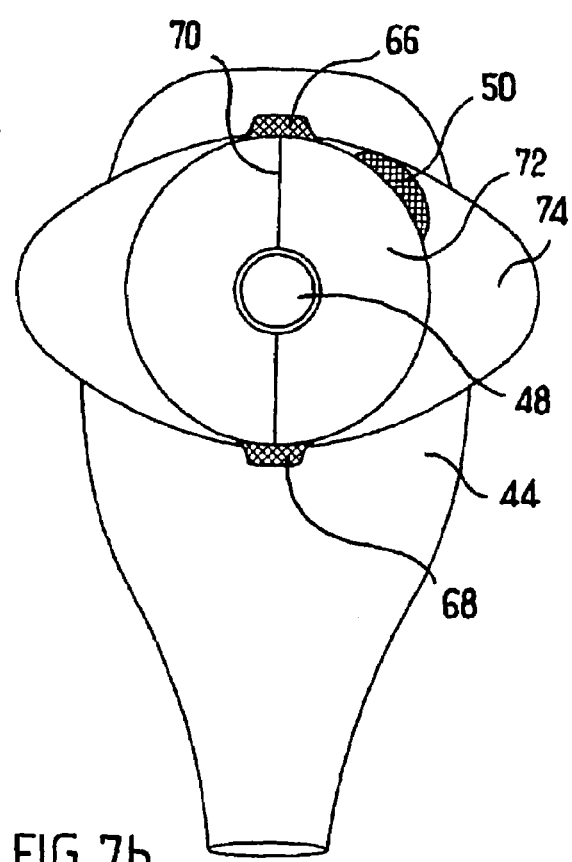

FIGS. 7a and 7b illustrate another embodiment in which the positioning before adhesive-bonding is provided, not by rotation about an articulation axis, but instead by the two parts of the connection being aligned in practice one relative to the other before the adhesive-bonding.

More precisely, as FIGS. 7a and 7b indicate, the fixing device has, either on the gum disc 32, or at the edge of the strip 4, two fixing elements 62, 64 of the hook and loop type, which are known under the commercial name "Velcro" and which can be diametrically opposed as illustrated. The pouch comprises, at corresponding locations of the connection portion, two complementary hook and loop type fixing elements 66, 68.

In this instance, since the fixing elements 62, 64 and 66, 68 are brought into co-operation when the adhesive surface of the connection portion of the pouch is not exposed and is still provided with the protective paper thereof, this protective paper has to be able to be removed after the auxiliary fixing elements have been brought into co-operation. Consequently, the protective paper this time comprises two separate portions which are folded in the manner of a folder in accordance with a diameter 70. Each portion comprises a semi-circular portion 72 which is arranged over half of the adhesive surface, in contact therewith, and another portion 74 which is connected thereto by means of simple folding and which is longer so that it extends to the outer side of the pouch and can be gripped. Consequently, when the fixing elements 62, 64, and 66, 68 have been fixed, the two portions 74 of protective paper extend at the sides, and they have only to be pulled in order to expose the adhesive surface which is then correctly positioned facing the strip 34 of the fixing device.

Figure 8A:
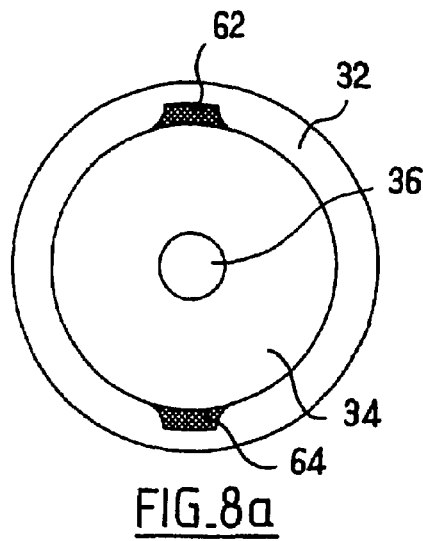
FIGS. 8a and 8b illustrate a fixing device and a pouch in which the complementary fixing elements are hook and loop type fixing elements which are fixed to the fixing device and to the body of the pouch itself, and the protective sheet of the adhesive layer comprises two portions which are folded in the manner of a folder, respectively.
Figure 8B:
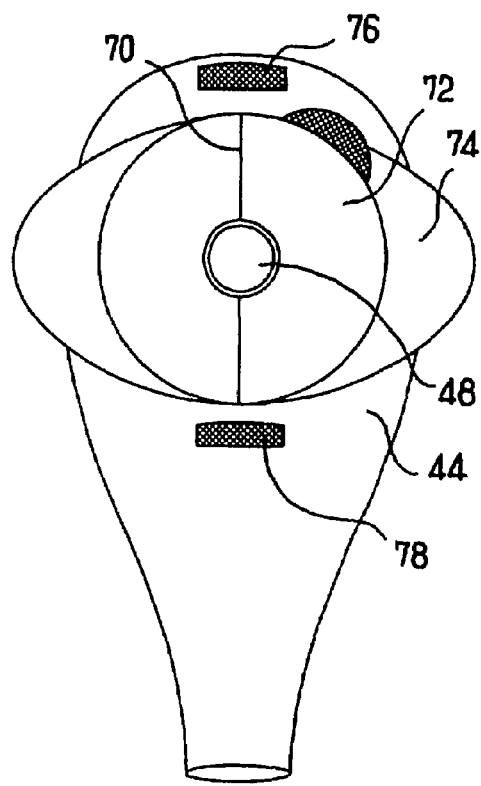

FIGS. 8a and 8b illustrate a variant in which the hook and loop type fixing elements 66 and 68, carried by the connection portion 46 of the pouch in FIG. 7b, are this time placed on the body 44 of the pouch, as indicated by the references 76 and 78. Operation is the same.

Figure 9:
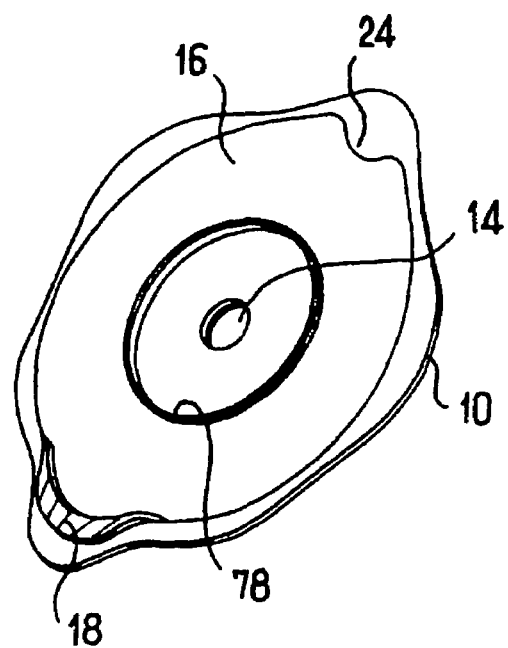
FIG. 9 illustrates an ostomy connection which is similar to that of FIGS. 1 to 3, after it has been positioned, but which comprises an additional fixing element which is constituted by a jaw which fits into the hole of the connection portion which is fixedly joined to the pouch.

FIG. 9 illustrates an additional variant. The fixing device 10 illustrated is similar to that of FIGS. 1 to 3 since it comprises a gum disc which is to be adhesively-bonded to the skin of the user, and a strip 16 which has a curved member 18 and a notch 24. The difference concerns the presence of an end-piece 80 which is fixedly joined to the gum disc, and which carries a jaw 78 which is intended to be fastened to the edge of the hole of the connection portion of the pouch, as illustrated in greater detail in FIG. 10.

This arrangement is very different from the device of the prior art since the length of the end piece is significantly reduced and the material thereof is very flexible, and it therefore does not bring about any discomfort. An improvement of this type can be used when the fixing force using adhesive-bonding is insufficient, for example, because the adhesive surface is very small or because the adhesive substance is not very robust.

Figure 11B:
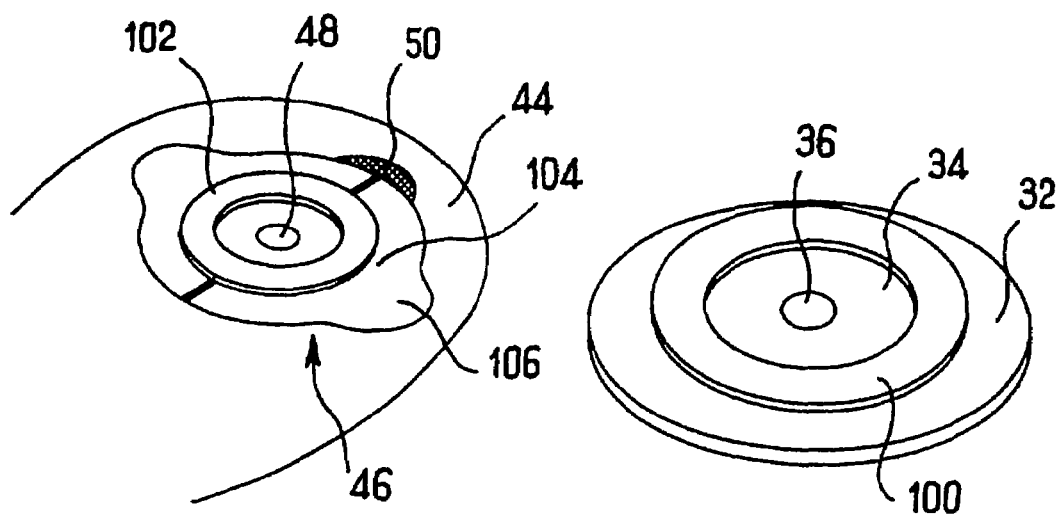
FIGS. 11a and 11b illustrate a fixing device and a pouch in which the complementary fixing elements are discs which can be fitted inside each other and which are fixedly joined, one to the fixing device and the other to the pouch, respectively.
Figure 11A:
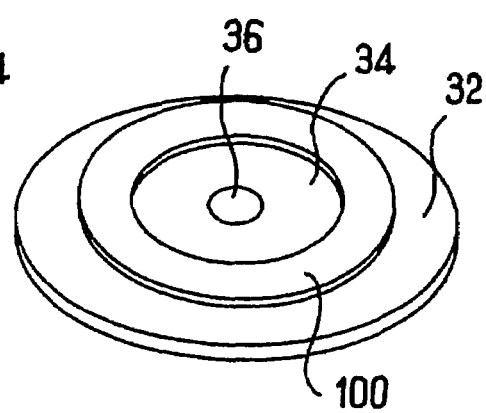

FIGS. 11a and 11b illustrate another embodiment in which the fixing device, which further comprises the gum disc 32, which delimits the hole 36, and the strip 34, further has a ring 100 of a resilient foam which is adhesively-bonded to the periphery of the strip 34. The connection portion 46 carries, at the surface thereof, around the hole 48, a ring 102 whose outer diameter is very slightly less than or equal to the inner diameter of the foam ring 100 of the fixing device. The pouch can therefore be readily positioned relative to the fixing device by the ring 102 being accommodated in the foam ring 100. In this embodiment, the adhesive surface of the connection portion 46 carries a protective paper 104 which is formed by two parts which are folded in the manner of a folder and which are each provided with a lug 106. After the ring 102 has been introduced into the ring 100, the protective paper 104 is pulled by the lugs 104 and exposes the adhesive surface which is then adhesively-bonded, preferably to a strip which is fixedly joined to the gum disc 32.

The ring 102 may be of any type whose adhesive properties are increased in the presence of aqueous liquid, and can form a secondary sealing zone which protects the main sealing zone.

The various embodiments described above relate to various aspects in which the sealing and the mechanical strength are substantially provided by the adhesive-bonding.

Figure 10:
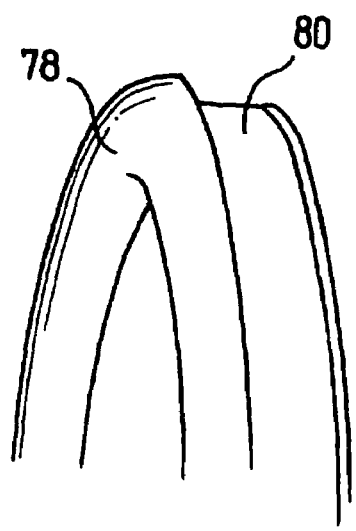
FIG. 10 illustrates the jaw shown in FIG. 9, drawn to an enlarged scale.

In specific embodiments, the mechanical strength may be increased, for example, by means of fitting (embodiments of FIGS. 10 and 11a, 11b).

A significant feature of the devices for fixing by means of adhesive-bonding according to the invention is the comfort afforded to users, since both the fixing device and the pouch can be very flexible and can adapt to the shape of the body.

Although embodiments have been described in which the strip 34 of the fixing device is not adhesive, and the connection portion 46 of the pouch is adhesive, the arrangement can be transposed. Furthermore, the adhesive-bonding can be carried out with an adhesive of the type having two components, one of which is placed on the strip and the other on the connection portion of the pouch.

The construction of the protective element of the adhesive surface has not been described since an element of this type is well known. A paper is generally used which is covered with a layer of silicone polymer placed in contact with the adhesive surface. Although, in the embodiments of FIGS. 7a, 7b and 8a, 8b, protective elements have been illustrated which are removed by being pulled in opposite directions, it is also possible for the tongues to extend in other directions, for example, midway between the horizontal axis and a hook and loop type fixing device.

The complementary fixing elements for the ostomy devices according to the invention may be used "blind", without it being necessary to see either the fixing device or the pouch. In this manner, the user, when he has introduced the tongue, fixed the push-buttons or introduced the clip, can press the adhesive portion against the strip with complete confidence without the risk of a fault in terms of alignment. The user can verify that adhesive-bonding is correct by pinching the strip and the connection portion which are adhesively-bonded using his fingers. If necessary, the user can ensure appropriate positioning by touching the strip and the connection portion whose peripheries correspond. The adhesive-bonding surface, and therefore the sealing, are optimised.

In all of the embodiments described, the disc carrying the adhesive surface of the pouch and the co-operating strip form a connection element which has been supposed to be of circular form, for reasons of ease of production. It has further been supposed that this disc was completely coated with adhesive substance. However, this arrangement presents a problem during use.

Reference is made to FIG. 12 which illustrates a connection element 110 of this type. When this has been adhesively-bonded and has to be detached, a detaching force is applied by the hand of the user who moves in the direction T of FIG. 12, this direction being parallel with the plane of the face of the connection element to be adhesively-bonded and being referred to below as the "detaching direction". The connection element is detached successively along a linear peeling face having an orientation which is generally perpendicular relative to the detaching direction T.

The intersection of the peeling face with the direction T, at various steps of the detaching operation, is indicated by the references A, B, E, C, and D in FIG. 12, these references being repeated in FIG. 13, which is a line which represents the variation of the total length of the peeling face in accordance with the position, marked on the X-axis. Below, this "total length of the peeling face" is the total, for each point of the peeling face, of the face segments which are generally orientated perpendicularly relative to the detaching direction and which are arranged at the surface of the connection element.

The line of FIG. 13, between the two ends A and D of the connection element in the detaching direction T, is such that the total length of the peeling face increases very rapidly, passes through a first maximum at B, then through a minimum at E, then through a second maximum at C, before being very rapidly cancelled out at D.

It is known that the detaching resistance force of a practically constant flexible adhesive surface is proportional to the length of the peeling face of the adhesive surface. In the case of the connection element of FIG. 12, the annular surface of the connection element is completely covered with adhesive of a substantially constant thickness and composition, and the detaching resistance force in the direction T is proportional to the total length of the peeling face. Consequently, the variation of the detaching resistance force is identical to that which is illustrated in FIG. 13. It increases very rapidly, passes through a first maximum at B, then through a minimum at E, then through a second maximum at C before being very rapidly cancelled out.

The detaching force applied to an adhesive connection element for an ostomy pouch is applied by a human being. This force must compensate for the retention force provided by the adhesive, which varies as indicated in FIG. 13. When the retention force is high (at B and C), the hand of the user must apply a great detaching force; if the retention force rapidly decreases, as after point C of FIG. 13, the detaching force applied by hand is greater than the retention force to such an extent that it brings about abrupt tearing. If it is an ostomy pouch, the abrupt separation of the pouch from the body causes pain (irritation of the skin) and a shaking of the pouch; it can bring about the projection of the contents out of the pouch or even the overturning of the pouch.

In advantageous embodiments of the invention, the total length of the peeling face, when the adhesive surface of the connection element is detached, is modulated so that it is substantially constant over at least the majority of the length of the connection element in the detaching direction.

More precisely, in the case of a substantially flat connection element which is covered with adhesive over at least a portion of one of the faces thereof and which is intended to be detached in one direction, the total length of the face for detaching by means of peeling, in a direction which is generally perpendicular relative to the detaching direction, is modulated so that it is substantially constant over the majority of the length of the connection element in the detaching direction.

In one embodiment, the face of the connection element is completely covered with adhesive, the shape of the connection element being suitable for providing the desired modulation of the total length of the peeling face.

In another embodiment, the face of the connection element is partially covered with adhesive, and it is the shape of the adhesive surface that is adapted in order to provide the desired constancy of the total length of the peeling face.

FIG. 14 illustrates the adhesive face of a connection element 112 according to the invention which is preferably constituted by a composition based on thermoplastic material, and a hole 114. This face of the connection element 112 is completely covered with a substantially constant thickness of adhesive. The connection element 112 has two portions which are symmetrical relative to the centre axis 116 thereof. The dimension of each of the two portions, measured in a direction perpendicular relative to the axis 116, is substantially constant over the entire length of the connection element, in the direction of the centre axis, except for at the ends.

The total length of the peeling face during a detaching operation is modulated so that it first increases rapidly towards a maximum value, then decreases towards a value which remains constant almost up to the other end when the position according to the axis 116 varies. In this portion, the detaching speed is constant for a constant applied force, and the detached portion forms an angle which is practically constant with the portion which is still adhesively-bonded.

This behaviour is confirmed by the graph of FIG. 15 which indicates that the force to be applied is first high, in order to provide a sense of security for the user, then decreases rapidly towards a substantially constant value which corresponds to a controlled detaching speed, before decreasing at the end.

FIG. 16 illustrates a variant of a connection element whose total length of the peeling face becomes constant more rapidly.

In the case of an ostomy pouch 118, as illustrated in FIG. 17, which can be more or less full, the risk of overturning or projecting a portion of the contents of the pouch is reduced.

The pouch 118 which is advantageously constituted by two films of flexible and transparent material welded at the edges thereof, for example, of thermoplastic material, is partially fixed to the connection element by means of welding or adhesive-bonding.

In another embodiment, the modulation of the total length of the peeling face, so that it has a substantially constant value over a large portion of the length in the detaching direction, is obtained by applying an adhesive to the connection element having a suitable surface which is not identical to that of the connection element. More precisely, portions which are not provided with adhesive remain on the surface of the connection element.

In another embodiment, the modulation of the total length of the peeling face takes into account other parameters which influence the peeling force, such as the variable rigidity of the connection element, the presence of other elements which are fixedly joined to the connection element, in particular a welded strip, etc. . . .

Of course, various modifications can be carried out by the person skilled in the art to the connections which have been described above purely by way of non-limiting example, without departing from the scope of the invention.

The invention claimed is:

1. An ostomy device connection which is intended to connect a collection pouch (42) to a fixing device (30) which is intended to be adhesively-bonded to the skin of a user, the connection serving:
   to transmit the weight of the collection pouch (42) to the fixing device (30),
   to position the pouch (42) relative to the fixing device (30) so that a hole (36) of the fixing device is in communication with a hole (48) of the collection pouch, and to provide sealing between the collection pouch (42) and the fixing device (30),
   the connection comprising a first connection portion (34) which is fixedly joined to the fixing device and a second connection portion (46) which is fixedly joined to the collection pouch,
   one of the connection portions having an adhesive surface which is covered before use by a removable protective sheet and the other connection portion having an adhesion strip, so that the two connection portions (14, 34, 46) can co-operate with each other by means of adhesive-bonding in a plane which is practically perpendicular relative to the axes of the holes (14, 36, 48) of the pouch and the fixing device, and the transmission of the weight of the collection pouch (42) and the sealing between the fixing device (30) and collection pouch (42) are provided by means of adhesive-bonding, the collection pouch (42) and the fixing device comprising complementary fixing elements which are intended to limit the possibilities for relative displace of the pouch (42) and the fixing device (30) so that the two connection portions have practically only one possible relative position when they are adjacent, this position corresponding to the alignment of the holes (36, 48) of the fixing device (30) and the collection pouch (42),
   wherein the protective sheet (72) of the adhesive layer has the feature of being able to be removed from the adhesive surface after the complementary fixing elements have been brought into co-operation,
   wherein the complementary fixing elements form an articulation device which delimits a pivot axis (40) remote from the holes of the fixing device (30) and the collection pouch (42), the protective sheet being practically entirely at only one side of the pivot axis.

2. The connection according to claim 1, wherein the complementary fixing elements comprise at least two push-buttons (38, 52) which are aligned along an axis.

3. The connection according to claim 1, wherein the complementary fixing elements comprise two elements (54, 56) which are fixedly joined to the fixing device (30) and the pouch (42), respectively, and which are able to provide mutual fixing by means of magnetic attraction.

4. The connection according to claim 1, wherein the complementary fixing elements comprise a tongue (20) which is fixedly joined to a first portion of the connection and a curved member (18) which is fixedly joined to the other portion of the connection.

5. The connection according to claim 1, wherein the complementary fixing elements comprise shaped portions (62, 64, 66, 70, 76, 78) of hook and loop type fabric which are fixedly joined to each of the connection portions (34, 46).

6. The connection according to claim 4, wherein the complementary fixing elements comprise at least a first element (18) which is arranged on a first connection portion, and a plurality of second elements (20) which are arranged on the other connection portion and which have positions which are angularly spaced-apart around the hole of the corresponding connection portion, the first element being able to co-operate with any one of the second elements.

7. The connection according to claim 6, wherein the portion which comprises the portion carrying the tongue (20) comprises a plurality of tongues having positions which are angularly spaced-apart around the hole thereof.

8. The connection according to claim 1, wherein the protective sheet (72) of the adhesive layer comprises at least two portions which are folded in the form of a folder whose folds are adjacent on the adhesive surface so that this adhesive surface is completely covered and the flap which is not adhesively-bonded to the adhesive surface has a gripping lug (74, 106) which extends beyond the limits of the adhesive surface.

9. The connection according to claim 1, wherein the portion having the adhesive surface is intended to be detached in one direction (T) after use, and the configuration of this adhesive surface is such that the total length of the face for detaching by means of peeling, in a direction which is generally perpendicular relative to the detaching direction, is modulated so that it is substantially constant over the majority of the length of the portion having the adhesive surface in the detaching direction.

10. The connection according to claim 1, wherein the complementary fixing elements comprise at least a first element (18) which is arranged on a first connection portion, and a plurality of second elements (20) which are arranged on the other connection portion and which have positions which are angularly spaced-apart around the hole of the corresponding connection portion, the first element being able to co-operate with any one of the second elements.

11. The connection according to claim 2, wherein the complementary fixing elements comprise at least a first element (18) which is arranged on a first connection portion, and a plurality of second elements (20) which are arranged on the other connection portion and which have positions which are angularly spaced-apart around the hole of the corresponding connection portion, the first element being able to co-operate with any one of the second elements.

12. The connection according to claim 3, wherein the complementary fixing elements comprise at least a first element (18) which is arranged on a first connection portion, and a plurality of second elements (20) which are arranged on the other connection portion and which have positions which are angularly spaced-apart around the hole of the corresponding connection portion, the first element being able to co-operate with any one of the second elements.

13. The connection according to claim 5, wherein the complementary fixing elements comprise at least a first element (18) which is arranged on a first connection portion, and a plurality of second elements (20) which are arranged on the other connection portion and which have positions which are angularly spaced-apart around the hole of the corresponding connection portion, the first element being able to co-operate with any one of the second elements.

* * * * *